United States Patent [19]

Budavari et al.

[11] Patent Number: 4,670,578

[45] Date of Patent: Jun. 2, 1987

[54] PROCESS FOR CRYSTALLINE SALTS OF L OR (S)-3-(3,4-DIHYDROXYPHENYL)-2-METHYLALANINE ESTERS

[75] Inventors: John Budavari, Watchung; Edward J. J. Grabowski, Westfield, both of N.J.

[73] Assignee: Merck & Co., Inc., Rahway, N.J.

[21] Appl. No.: 527,525

[22] Filed: Aug. 29, 1983

[51] Int. Cl.$^4$ .................................... C07C 101/77
[52] U.S. Cl. .................................................. 560/40
[58] Field of Search ................ 560/40; 562/446, 401

[56] References Cited

U.S. PATENT DOCUMENTS

| | | | |
|---|---|---|---|
| 3,983,138 | 9/1976 | Saari | 560/40 |
| 3,988,341 | 10/1976 | Saari et al. | 560/40 |
| 4,016,288 | 4/1977 | Scriabine et al. | 560/40 |
| 4,051,169 | 9/1977 | Saari | 560/40 |
| 4,265,874 | 5/1981 | Bonsen et al. | 424/15 |

OTHER PUBLICATIONS

Saari, et al., J. Med. Chem. 21, 746 (1978).

*Primary Examiner*—Natalie Trousof
*Assistant Examiner*—Bruce D. Gray
*Attorney, Agent, or Firm*—Alice O. Robertson; Mario A. Monaco

[57] ABSTRACT

Crystalline salts of (R,S)-pivaloyloxyethyl esters of (S)-3-(3,4-dihydroxyphenyl)-2-methylalanine and processes for their preparation are disclosed.

3 Claims, No Drawings

PROCESS FOR CRYSTALLINE SALTS OF L OR (S)-3-(3,4-DIHYDROXYPHENYL)-2-METHYLALANINE ESTERS

The present invention is concerned with certain salts of (R,S) pivaloyloxyethyl esters of L or (S)-3-(3,4-dihydroxyphenyl)-2-methylalanine in a crystalline form and to processes for their preparation.

BACKGROUND OF THE INVENTION

L or (S)-3-(3,4-dihydroxyphenyl)-2-methylalanine, more commonly known as methyldopa, is a well-recognized antihypertensive agent which is generally administered orally in the form of capsules, pellets, or emulsions. Certain esters of methyldopa have been found to be of greater potency, Saari et al., J. Med. Chem. 21, 746 (1978). One of the esters found to be of higher potency is the 1-pivaloyloxyethyl ester of (S)-3-(3,4-dihydroxyphenyl)-2-methylalanine. Preparation and pharmaceutical applications of these pivaloyloxyethyl esters are also described in U.S. Pat. Nos. 3,983,138; 3,988,341; 4,016,288 and 4,051,169. The latter patent also teaches that both isomers arising as a result of the chiral center in the substituted alkyl portion of the ester are active pharmacologically. Subsequent work has supported the efficaciousness of the pivaloyloxyethyl ester and the desirability of employing this highly effective ester product in special means for administration such as in controlled delivery systems. Controlled delivery systems include not only a delayed delivery method such as enteric coated tablets but also and particularly, delivery in devices such as an osmotic pump for controlled and continuous release of drugs. A representative device is described in U.S. Pat. No. 4,265,874. For efficient and effective use in such device, it is highly desirable that the drug be in a pure crystalline form, and further exhibit appropriate solubility properties for controlled release in an aqueous environment. However, the pivaloyloxyethyl ester tends to be unstable even when obtained in a crystalline form. Thus, it is desirable to provide a method for obtaining the pivaloyloxyethyl esters of methyldopa not only in a crystalline form, but also in a stable form. Further, it is desirable to have the ester in a form having solubility properties adaptable for controlled release in an aqueous environment. Moreover, since as taught in U.S. Pat. No. 4,051,169, both isomers of the esters are pharmacologically active, it is desirable to provide for a method in which both isomers may be obtained in crystalline form without undue difficulty.

STATEMENT OF THE INVENTION

According to the present invention there has been discovered certain crystalline salts of the diastereomeric (R,S) mixture of pivaloyloxyethyl esters of (S)-3-(3,4-dihydroxyphenyl)-2-methylalanine which are stable to heat and compression, encountered during formulation and/or storage, and which have solubility properties suitable for use in osmotic delivery devices for controlled and continuous release of drugs. There has further been discovered a process for directly obtaining crystalline salts of both diastereomeric isomers in a single operation, i.e., without need for the usual steps of first causing crystal formation of one isomer, removing the crystals from the mixture and thereafter causing the crystal formation of the second isomer. A further aspect of the process is the preparation of these crystalline (R,S) salts from the reaction mixture obtained in the synthesis of (R,S) esters. Another aspect is a process for simultaneous preparation of a certain group of (R,S) salts. Other aspects include pharmaceutical compositions comprising said crystalline ester salts suitable for use in the control of hypertension.

DETAILED DESCRIPTION OF THE INVENTION

The crystalline (R,S) salts of the present invention may be represented by the formula:

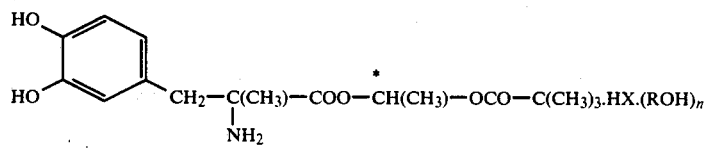

I wherein HX represents the acid forming the salt with the ester base; ROH represents the solvent of the solvate and n is a number of from ½ to 3. Although the salt is written above and hereinafter in the specification as an acid addition salt, it is to be understood that the salt formation takes place with the proton attaching at the amino nitrogen and may be written as follows:

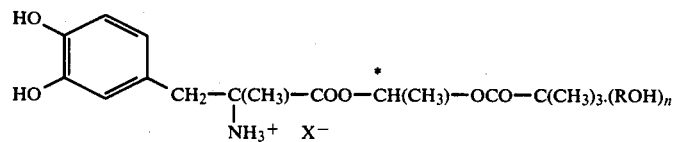

II

In the foregoing formula, X represents the residual group remaining after removal of a proton from the acid, HX, and R in ROH represents hydrogen or lower alkyl depending on whether the solvent forming the solvate is alcohol or water; and n is as hereinbefore defined.

The acids which are to be employed to form the desired salts are oxygenated acids. By "oxygenated acids" is meant an inorganic or organic acid containing an oxygen atom to which a proton is attached. Preferred inorganic acids include phosphoric and sulfuric acids. Preferred organic acids include tartaric acid, maleic acid, malonic acid, and the like. Some of the organic acids have chiral centers; when such acids are employed it is desirable to employ a single enantiomorph. More than one acid may be employed with the same ester to form salts of mixed acids. Thus, by using phosphoric acid and tartaric acid, a phosphate/tartrate salt mixture may be obtained. In such cases, HX in Formula I represents two acids and also may be designated $HX_1.HX_2$ where $X_1$ and $X_2$ are different anionic groups.

The solvate forming solvents contemplated by the present invention are non-acidic, hydroxylated solvents, particularly alkanols and water. Thus, ROH includes water, ethanol, pentanol-1, pentanol-2, isopropanol, propanol, methanol and the like. Preferred solvates are ethanolate and hydrate from ethanol and water, respectively. These solvates are also preferred for use in osmotic delivery devices.

Novel crystalline salts of the present invention named as acid addition salts and in which (R,S)-1-pivaloyloxyethyl (S)-3-(3,4-dihydroxyphenyl)-2-methylalaninate is designated (R,S)-POE ester methyldopa include crystalline (R,S)-POE ester methyldopa.$H_3PO_4.H_2O$; (R,S)-POE ester methyldopa.$H_3PO_4.C_2H_5OH$; (R,S)-POE ester methyldopa.(+)tartaric acid.$H_2O$; (R,S)-POE ester methyldopa.$H_3PO_4.CH_3OH$; (R,S)-POE ester methyldopa.$H_2SO_4.C_2H_5OH$; (R,S)-POE ester methyldopa. $H_2SO_4.H_2O$; (R,S)-POE ester methyldopa. (−)tartaric acid.$H_2O$; (R,S)-POE ester methyldopa.DL-tartaric acid.$H_2O$; (R,S)-POE ester methyldopa.meso-tartaric acid.$H_2O$; (R,S)-POE ester methyldopa.maleic acid.$H_2O$.

Especially preferred salts for use in pharmaceutical compositions are (R,S)-1-pivaloyloxyethyl (S)-3-(3,4-dihydroxyphenyl)-2-methylalaninate (+)-tartaric acid/phosphoric acid (3/1) monohydrate and (R,S)-1-pivaloyloxyethyl (S)-3-(3,4-dihydroxyphenyl)-2-methylalaninate phosphoric acid monoethanolate.

The salts may have an apparent fractional amount of water of hydration or solvent of solvation attributable either to mixtures of solvated and unsolvated salts or the solute "bridging" two salt molecules. The extent of solvation is preferably in the range of ½ to 1; i.e., n is from ½ to 1.

The process may be applicable to formation of salts from other acids but for the intended purposes, the foregoing novel crystalline salt mixtures are a preferred embodiment of the present invention.

As can be seen in Formula I, there are two points in the formula which may be designated as chiral centers. One point is on the amino acid portion, specifically the carbon atom to which the amino nitrogen is attached and the other is in the hydroxy compound portion of the ester, specifically the carbon atom attached to the oxygen of the ester group and designated with an asterisk (*). Since the pharmacologically active amino acid, methyldopa, is always the L or (S) form of 3-(3,4-dihydroxyphenyl)-2-methylalanine, only the L or (S) form of the acid is employed in the preparation of the ester, and the chiral center on the amino acid portion of the above formula is always (S) and does not contribute to the formation of isomeric mixtures during salt formation. Since 1-chloroethyl pivalate used in the preparation of 1-pivaloyloxyethyl ester (POE ester) of methyldopa has a chiral center, the resulting esters are a mixture of (R) and (S) diastereomers, and the salts resulting from the esters would also be a mixture of diastereomers. As has been previously established, both isomers are pharmacologically active, thus, salts of both isomers are desired. However, as generally known, salts of diastereomers not only separate in a stepwise manner but almost always require isolation and removal of the crystals of one isomer before separation of the second isomer can be made to occur. Moreover, separation of the second isomer usually requires extensive manipulative procedures; however, if such procedures are not taken then about one-half of the ester is unutilized and wasted, a commercially unfeasible operation.

Thus, it was wholly unexpected that according to the process of the present invention a crystalline mixture of salts corresponding to the mixture of (R) and (S) POE esters of (S)-3-(3,4-dihydroxyphenyl)-2-methylalanine may be produced without the need for first isolating the salt of one of the ester isomers, thereby making it possible to avoid, on the one hand, an onerous and expensive procedure which would be necessitated by first isolating one isomer and using extensive manipulative procedures to recover the second isomer, and on the other hand, a wasteful procedure of forming the salt of a single ester isomer and discarding the mother liquor. A further aspect of the present invention is a process not only of preparing a crystalline mixture of salts without the need for first isolating one isomer but also for preparing a crystalline mixture of salts of the isomers from the reaction mixture formed in the ester synthesis without the need for recovering the esters from the reaction medium as a solid.

In the process of the present invention, the crystalline salts are prepared by reacting an isomeric mixture of esters, namely (R,S)-1-pivaloyloxyethyl (S)-3-(3,4-dihydroxyphenyl)-2-methylalaninate (hereinafter also designated R,S-POE ester base) and a salt forming acid in an organic solvent. The organic solvent may be the solvate forming solvent as hereinbefore defined or other common inert organic solvent, water-immiscible or miscible. For consistent good results, the reaction preferably is carried out in a substantially water-immiscible organic solvent with inclusion of a very small amount of a hydroxylated solvent. Thus, the preferred process contemplated for preparing a diastereomeric salt mixture of 1-pivaloyloxyethyl ester of (S)-3-(3,4-dihydroxyphenyl)-2-methylalanine comprises (a) forming a solution of (R,S)-1-pivaloyloxyethyl (S)-3-(3,4-dihydroxyphenyl)-2-methylalaninate in a non-polar substantially water-immiscible organic solvent, (b) adding thereto a solvate forming hydroxylated solvent and a salt forming oxygenated acid, and (c) intimately contacting the mixture preferably under an atmosphere of nitrogen for time sufficient to cause crystallization of the salts of R and S isomers.

The reaction may be carried out entirely at ambient temperature. However, generally after initial crystal formation subsides, it is desirable to cool the reaction mixture and maintain the mixture in the cooled state to complete the reaction with the formation of the salts of R,S-POE ester base in good yields. Generally yields of 80 percent or greater may be obtained.

By the expression "ester base" is meant POE ester as hereinbefore defined but used in the context of conversion to a salt or vice-versa. The reactant R,S-POE ester base is preferably pure or purified ester base. The ester base may be obtained by the reaction of (R,S)-1-chloroethyl pivalate with (S)-3-(3,4-dihydroxyphenyl)-2-methylalanine as described in the aforecited Saari et al. paper and thereafter purified or may be prepared more directly as a crystalline ester as described in copending application Ser. No. 353,697, filed Mar. 1, 1982 in the name of John Budavari and also described hereinafter in connection with the procedure for preparation of the salts from a reaction mixture obtained in the preparation of the esters. For certain salts, it is important that the ester base be of a purified crystalline material. For others, while not as important that crystalline ester base be employed, it is advantageous to subject the ester base to purification procedures which is described hereinafter.

When the starting ester base is of at least 95 percent purity and the salt is to be an alkanolate the reaction may be carried out in the absence of a water-immiscible organic solvent with the alkanol serving as a dispersion medium.

When the reaction is carried out according to the preferred process in a substantially water-immiscible organic solvent, the salt forming acid and the solvate solvent may be added successively, simultaneously or in the form of a solution of the acid in the solvate solvent. It is preferably added in the form of a solution of the acid in a solvate solvent. Moreover, it is preferably added to the reaction medium in a dropwise manner.

Suitable solvents for the substantially water-immiscible reaction medium in the salt preparation include toluene and other alkylated aromatic hydrocarbons, halogenated aliphatic and aromatic hydrocarbons, esters, such as ethyl acetate, isopropyl acetate and the like, and ethers, such as diethyl ether, diisopropyl ether and the like. Preferred solvents are esters such as ethyl acetate and alkylated aromatic hydrocarbons such as toluene.

The actual amount of solvent depends on the solvent employed and the solubility of the POE ester base in the solvent. It is highly desirable that the amount be such that the ester base not exceed about 10 percent by weight. Generally an amount to provide a 2 to 5 weight percent solution of the ester base in solvent would be considered satisfactory.

When the ester base is in a crude or unpurified state, preliminary purification steps are employed prior to the preparation of salt crystals utilizing the ultimate reaction solvent. The purification may be carried out by thoroughly mixing the crude ester base with the solvent to be employed in the salt preparation to dissolve the ester base therein, and then separating the insoluble material (predominantly methyldopa) by suitable manipulative procedures such as filtering, washing, and the like. Thereafter, the ester base solution is employed in the foregoing crystal salt formation process, after first taking appropriate steps, if necessary, to bring the solution into an appropriate concentration range for reaction.

The reaction is preferably carried out in an atmosphere of nitrogen or other inert gas.

The temperature for crystallization varies from ambient temperature to $-25°$ C. Ambient temperature is meant a temperature in the range from about 15° C. to about 30° C. The preparation of salts as alkanolates, particularly from mineral acids such as phosphoric acid, may be carried out entirely at ambient temperature. However, it is generally preferable to keep the temperature below at least about 25° C. so some cooling as necessary is usually employed. After initial separation of crystals cooling is preferably employed to temperatures near 5° C. and below to as low as about $-25°$ C. to induce further separation of crystals. Crystallization occurs without removal of the crystals initially formed.

Although not essential, the reaction mixture usually is seeded with a salt prior to each crystallization. While any conventional means for inducing crystallization may be employed, crystallization is greatly facilitated by seeding. Suitable seeds are not only previously prepared identical salt solvate but also any solvate of the corresponding crystalline salt.

After completion of the reaction, the R,S salt mixture may be recovered by filtration and purified, if desired, by washing with solvent and drying under reduced pressure.

During the course of the reaction, the formation of the crystalline salts may be followed by thin layer chromatography (TLC) by sampling the crystals, washing with solvent, and placing on silica gel plates, developing with solvent mixture, preferably 60:25:10:5-$C_2H_5OCOCH_3$:n-$C_4H_9OH$:HCOOH:$H_2O$ and visualizing with $I_2$. Alternatively, samples may be taken and checked by optical rotation.

The process is also adaptable to the preparation of salts of more than one acid. For the preparation of salts of multiple acids, a crystalline R,S mixture of salts from a single acid is first prepared as above described. Thereafter, the second acid and the solvate forming solvent, preferably as a solution of acid in solvent, are added, usually directly to the crystalline mixture of salts from the first acid, and the resulting mixture stirred with cooling, generally below 0° C. to obtain crystals of the second salt to obtain an R,S mixture of salts derived from two acids, $HX_1.HX_2$. After substantial completion of the crystallization, the crystalline product of mixed salts are recovered by filtration, washed with solvent and dried.

In the preparation of the mixed salts, temperature control at the time of formation of the second salt is particularly critical. It should not be permitted to exceed about 25° C. and is generally carried out below 0° C. or lower and as low as $-25°$ C.

An important aspect of the process of the present invention is the preparation of the salts of the R,S-POE esters directly from the crude reaction mixture obtained in the synthesis of (R,S)-1-pivaloyloxyethyl (S)-3-(3,4-dihydroxyphenyl)-2-methylalaninate by alkylation of (S)-3-(3,4-dihydroxyphenyl)-2-methylalanine with 1-chloroethyl pivalate. In the preparation of the salts from the crude alkylation reaction mixture, the reaction solvent from the alkylation step is first replaced with a water-immiscible organic solvent, the resulting solution freed of acid impurities and then used to prepare the crystalline salt mixture of R,S-POE ester in the manner previously described for the preparation of crystalline salt mixture starting from isolated R,S-POE ester of methyldopa.

The POE ester base containing reaction mixture is that which may be obtained by mixing together and reacting substantially equimolar proportions of methyldopa and 1-chloroethyl pivalate in an aprotic solvent in the presence of a molecular sieve, preferably in an atmosphere of nitrogen, and preferably with moderate heating over a period of time sufficient to complete the reaction with the formation of the desired ester as described in copending application of John Budavari previously referred to.

In this process, substantially equimolar amounts of methyldopa and 1-chloroethylpivalate, and a molecular sieve, in an amount preferably in the range of 30 to 40 grams per 100 grams of methyldopa, are placed in an aprotic solvent, said solvent being employed in an amount of from about 1 to 10 milliliters for each gram of methyldopa, and the mixture stirred at temperatures in the range of from about 25° C. to about 150° C., preferably about 70° to 100° C. for time sufficient to complete the reaction with the formation of the POE esters of methyldopa.

Suitable molecular sieves are of crystalline metal aluminosilicates in powder, pellets and beads. They are readily available commercially and are referred to in pore size (angstrom) designations such as 3A,4A,-5A,13X and the like.

The "aprotic solvent" in which the reaction is carried out is a material which is liquid under reaction conditions, which at least partially dissolves the reactants and which does not readily yield or accept a proton. It is preferably miscible with water. Solvents suitable for carrying out the reaction include dimethyl sulfoxide, formamide, tetramethylurea, tetraethylurea, cyclic ureas, N,N-dialkylacetamides, hexamethylphosphoramide, tetrahydrofuran, N-alkyl-pyrrolidinones, acetonitrile, 1,3-dimethyl-2-imidazolidinone, 1,3-dimethyl-3,4,5,6-tetrahydro-2(H)-pyrimidinone, and the like and mixtures thereof.

The reaction mixture obtained as above described, containing the R and S POE esters of methyldopa (ester bases), and also containing unreacted starting materials, by-products, molecular sieve and reaction solvent, is first diluted with a water-immiscible organic solvent and then washed with an aqueous base to remove undesired acidic material. The aprotic solvent is also removed in the washing process, having been replaced by the water-immiscible organic solvent. To the washed solution containing the ester bases, there is added a salt forming acid corresponding to the salt desired and a hydroxylated solvent, and the mixture stirred to obtain crystalline solvated salt of (R,S)-1-pivaloyloxyethyl ester of methyldopa in the manner previously described for the process starting from an isolated isomeric ester base mixture. The product salt may be purified by washing with solvent and drying under reduced pressure.

The base used above for washing the ester bearing solution may be any water-soluble, organic solvent-insoluble base, and is preferably an inorganic base. A preferred base is sodium bicarbonate, although sodium carbonate, sodium chloride, calcium chloride and the like also may be employed.

Alkanolate salts, particularly those derived from inorganic acids, may be obtained in a process whereby purified POE ester base mixture and appropriate acid are admixed in excess alkanol in the presence of a minor amount of water. By "excess" is meant more than the molar amount which would be necessary to form an alkanolate. The amount should be that sufficient to permit smooth mechanical mixing of a slurry of reactant ester and product salt or that sufficient to form a solution when a minor amount of water is added. In this process, the desired R,S mixture of salts are substantially instantaneously formed as alkanolates in substantially crystalline form. Sometimes some amorphous material may coprecipitate but these are readily convertible to crystalline salts. However, the process applicable to all solvates is one in which the ester base and acid are reacted in a water-immiscible organic solvent as previously described.

The foregoing procedures and modifications described provide a simple and economical process for obtaining crystalline salts which can be a means for supplying 1-pivaloyloxyethyl (S)-3-(3,4-dihydroxyphenyl)-2-methylalaninate in a form suitable for special drug delivery systems such as, for example, an osmotic pump. Thus, the salts so prepared show good solubility characteristics and osmotic pressure properties in aqueous systems which can be correlated with compositions suitable for use in osmotic pumps. The solubility properties are outstanding and highly unexpected since the salts generally found to be useful for enhancing solubility such as hydrochloride solvates do not exhibit these outstanding properties. The solvate salts derived from oxygenated acids and POE esters of methyldopa have been found to increase the solubility of methyldopa in aqueous media to the extent of 15 times and more. Thus, methyldopa has a solubility of 10 grams per liter, whereas the solvated phosphate salt mixture of (R,S)-POE ester of methyldopa has a solubility in the range of 57 to 197 grams per liter and the solvated tartaric acid salt mixture has a solubility in the range of 156 to 383 grams per liter. (The solubility of the salts has been found to be system dependent, i.e., dependent on the amount of salt present and the relative amount of the (R) and (S) salts.) In addition, the POE ester salts also have been found to have advantageous properties over the POE ester bases which tend to be unstable when subjected to an aqueous environment or to mechanical stress such as grinding.

Pharmaceutical compositions comprising the salts of the present invention constitute an aspect of the present invention. However, since the usefulness of the novel crystalline salts of the present invention is the provision of a means for rendering 1-pivaloyloxyethyl (S)-3-(3,4-dihydroxyphenyl)-2-methylalaninate adaptable to special methods of administration, as well as providing a superior form of the drug, and not to impart a new pharmacological activity, the amounts to be employed in pharmaceutical compositions are readily ascertainable by the skilled artisan from the literature including the previously cited publication in the Journal of Medicinal Chemistry. For use in an osmotic delivery device the salts may be formulated employing materials suitable for methyldopa POE ester salts in their pharmaceutical application but prepared in a manner similar to that described in U.S. Pat. No. 4,265,874 for a different drug and use.

While it is necessary to provide a product with certain purity and solubility properties for use with delivery devices, the products of said purity and solubility are also useful in conventional modes of administration and also may be employed in more conventional pharmaceutical compositions for reducing hypertension.

For conventional methods of administration, the salts of the present invention may be contained in compositions preferably administered in unit dosage form such as tablets, pills, capsules, powders, granules, sterile parenteral solutions or suspensions, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums and functionally similar materials as pharmaceutical diluents or carriers. The tablets or pills of the novel compositions can be laminated or otherwise compounded to provide a dosage form providing the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The compounds are also useful when administered in the form of suppositories or with a penetrant such as dimethyl sulfoxide.

The liquid forms in which the novel composition of the present invention may be incorporated for administration include suitably flavored emulsions with edible oils, such as cottonseed oil, sesame oil, coconut oil, peanut and the like, as well as elixirs and similar pharmaceutical vehicles. Suitable dispersing or suspending agents for aqueous suspensions include synthetic and natural gums, such as tragacanth, acacia, alginate, dextran, sodium carboxymethylcellulose, methylcellulose, polyvinylpyrrolidone, gelatin and the like. Sterile suspensions or solutions are required for parenteral use. Isotonic preparations containing suitable preservatives are also highly desirable for injection use.

The term single dosage form as used in the specification refers to physically discrete units suitable as unitary dosage for warm-blooded animal subjects, each unit containing a predetermined quantity of active material calculated to produce the desired therapeutic effect in association with the required pharmaceutical diluent, carrier or vehicle. The specifications for the novel single dosage forms of this invention are dictated by and are directly dependent on (a) the unique characteristics of the active material and the particular therapeutic effect to be achieved, and (b) the limitations inherent in the art of compounding such an active material for therapeutic use in warm-blooded animals as disclosed in detail in this specification. Examples of suitable oral single dosage forms in accord with this invention are tablets, capsules, pills, powder packets, granules, wafers, cachets, teaspoonfuls, dropperfuls, ampules, vials, segregated multiples of any of the foregoing, and other forms as herein described.

The following examples illustrate the invention but are not to be construed as limiting.

REPRESENTATIVE PREPARATIONS OF SEED CRYSTALS

Since crystal formation is facilitated by seeding, it has been found advantageous to first prepare seed crystals. The procedures employed have been either to carry out a small preparation using about 10 grams of POE ester and producing the crystals via spontaneous crystallization or to effect a solvent of crystallization exchange.

Illustrative of a small scale of preparation is that of phosphoric acid ethanolate salt from POE ester: 10 grams of methyldopa (R,S)-POE ester, 3.4 grams of 85 percent phosphoric acid are added to a mixture of 70 milliliters of toluene and 35 milliliters of ethanol at room temperature, then allowed to stand at 5°–10° C. overnight to obtain crystals of (R,S)-1-pivaloyloxyethyl (S)-3-(3,4-dihydroxyphenyl)-2-methylalaninate, phosphoric acid monoethanolate salt product.

Illustrative of small scale preparation of phosphoric acid ethanolate salt via solvent of crystallization exchange: 10 grams of (R,S)-POE ester phosphoric acid salt monohydrate from an earlier synthesis is dissolved in 200 milliliters of hot anhydrous ethanol and the mixture allowed to cool to room temperature whereupon crystal formation starts. The mixture is allowed to stand overnight to complete the crystal formation and separation of (R,S)-1-pivaloyloxyethyl (S)-3-(3,4-dihydroxyphenyl)-2-methylalaninate, phosphoric acid monoethanolate salt product.

EXAMPLE 1

(R,S)-1-Pivaloyloxyethyl (S)-3-(3,4-Dihydroxyphenyl)-2-methylalaninate, Phosphoric Acid Monoethanolate Salts A. Preparation of the POE Ester Base Under an atmosphere of nitrogen, 425 grams (2.0 moles) of (S)-3-(3,4-dihydroxyphenyl)-2-methylalanine (methyldopa), 352 milliliters (2.0 moles) of 1-chloroethyl pivalate, 142 grams of 4A molecular sieve (1/16" pellets), and 850 milliliters of tetramethylurea were mixed together, heated to 75° C., and thereafter maintained at temperatures in the range 70°–75° C. for 30 to 36 hours. During this period, the methyldopa dissolved with the formation of (R,S)-1-pivaloyloxyethyl ester of methyldopa. Thereafter, the reaction mixture containing ester was cooled to 25° C. and diluted with 3500 milliliters of toluene. The organic molecular sieve containing layer was then washed with three 4.5 liter portions of saturated sodium bicarbonate solution at 15°–20° C. and filtered to clarify the solution to recover organic solution containing POE ester of methyldopa.

B. Preparation of the Salt Product

To the organic solution there was added about 3 liters of ethanol, followed by 168 grams (1.46 moles) of 85 percent phosphoric acid and 4 grams of methyldopa R,S,-POE ester phosphoric acid monoethanolate seed, and the mixture aged by stirring at about 20°–25° C. for about 20 hours to obtain an R,S-1-pivaloyloxyethyl S-3-(3,4-dihydroxy-phenyl)-2-methylalaninate, phosphoric acid salt, monoethanolate product. The product was washed twice with 400 milliliters of ethanol-toluene and dried in vacuo to obtain 375.4 grams (38.8 percent yield) of a purified crystalline product. Analytical results were as follows:

KF (Karl Fischer) =0.50 percent ($H_2O$)

GLC=8.67 percent EtOH (9.53 percent theory for 1 mole EtOH)

Titration $HClO_4$=99.9 (corr. for EtOH and $H_2O$); NaOH=100.0 (corr. for EtOH and $H_2O$)

LC=97.6 percent (weight percent; corr. for EtOH and $H_2O$) $[\alpha]_{365}^{25} = -18.2°$ (38.6 percent S-isomer; 61.4 percent R-isomer, based on rotation of −41.7° for pure S-isomer and +14.3° for pure R-isomer).

EXAMPLE 2

(R,S)-1-Pivaloyloxyethyl (S)-3-(3,4-Dihydroxyphenyl)-2-methylalaninate, Phosphoric Acid Monoethanolate Salts Approximately 200 grams (0.59 mole) of methyldopa, R,S-POE ester (97 percent purity) followed by 68 grams (0.59 mole) of 85 percent phosphoric acid were charged to a mixture of 1,400 milliliters of toluene and 700 milliliters of ethanol at 21° C. to obtain a light amber solution of the mixture. The solution was then seeded with a previously prepared POE ester salt whereupon crystal formation occurred with precipitation of POE ester salt. The crystalline slurry was then allowed to stand (aged) at 5°–10° C. for about 16 hours to allow crystallization of the isomeric POE ester salt; thereafter, the mixture was filtered and washed with 650 milliliters of toluene: ethanol (2:1) followed by 1200 milliliters of hexane and dried under a nitrogen atmosphere, in vacuo at 25° to obtain 267 grams (93 percent yield) of methyldopa R,S-POE ester phosphate ethanolate.

Analytical results were as follows:

KF 0.59 percent
GLC=8.52 percent EtOH
Titration $HClO_4$=100.4 percent
NaOH=99.3 percent
L.C. 98.2 percent (weight percent; corr. for EtOH and $H_2O$)

Elemental Analysis: Calculated for $C_{17}H_{25}NO_6 \cdot H_3PO_4 \cdot C_2H_5OH$: C, 47.20; H, 7.10; N, 2.90; P, 6.41 (Corr. for EtOH and $H_2O$).

Found C, 46.62; H=7.19; N, 2.88; P, 6.34. $[\alpha]_{365}^{25} = -12.6°$ (about 52 percent (S) isomer).

EXAMPLE 3

(R,S)-1-Pivaloyloxyethyl
(S)-3-(3,4-Dihydroxyphenyl)-2-methylalaninate
Phosphoric Acid Monohydrate Salts 200 grams (0.589 mole, 96.4 percent purity) of (R,S)-POE ester base mixture in 4.9 liters of ethyl acetate was stirred under nitrogen at 20°–25° C. for about twenty minutes and the mixture then filtered to remove insoluble material which was primarily methyldopa. The latter was washed with two 250 milliliter portions of ethyl acetate and the wash added to the solution containing the base mixture which then amounted to 5.45 liters. To this solution was added dropwise over about a 15 minute period, a solution of 39.2 milliliters (0.571 mole corrected for 3 percent methyldopa impurity) of 85 percent phosphoric acid in 58.8 milliliters of water. The addition funnel was rinsed with 430 milliliters of ethyl acetate and the combined ethyl acetate solution (5.98 liters) was seeded with a previously prepared (R,S)-POE ester phosphate salt whereupon crystallization started. The crystallizing mixture was stirred at room temperature for 2 hours, then cooled to 0° C. over a 2 hour period. The crystals which formed at room temperature were primarily those of the S-isomer salt as determined by sampling the crystals and checking the TLC (thin layer chromatography) of the solid (system employed: silica gel plates 60:25:10:5-EtOAc:n-BuOH:HCOOH:$H_2O$; $I_2$ visualization, $R_f$ -S isomer=0.6; $R_f$ R isomer=0.7). Thereafter the mixture was further cooled to a temperature of −10° C. and allowed to stand at this temperature to crystallize the remaining ester salt.

During this period, the progress of the crystallization was followed by TLC and rotation. After about 19 hours total reaction time, the white crystalline (R,S)-1-pivaloyloxyethyl (S)-3-(3,4-dihydroxyphenyl)-2-methylalaninate phosphoric acid monohydrate salt was recovered by filtration. (A total solids determination of the filtrate indicated that about 10 percent of the product was still in the filtrate.) The white crystalline salt was washed with three 490 milliliter portions of ethyl acetate and dried to a constant weight of 231 grams (corrected for 2 grams of seed) which amounted to a yield of 86 percent (89.3 percent when corrected for the purity of the starting (R,S)-POE ester base). The salt had a melting point of 117.5°–119.5° (dec.).

Results of analyses of the product were as follows:
KF =4.78 percent (theory 3.95 percent)
Titration ($HClO_4$) =99.3 percent uncorr.
UV A% 280 nm =62.6
LC =73 weight percent compared to standard POE base; (98.7 weight percent corrected for KF)
X-ray - crystalline
$[\alpha]_{365}^{25}$ nm= −11.6° 53.9 percent S-isomer; 46.1 percent R-isomer Elemental analyses: Calculated for $C_{17}H_{25}NO_6 \cdot H_3PO_4 \cdot H_2O$ (455.5). C, 44.84; H, 6.64; N, 3.08; P, 6.80. Found: C, 44.55; H, 6.56; N, 2.83; P, 6.58.

EXAMPLE 4

(R,S)-1-Pivaloyloxyethyl
(S)-3-(3,4-Dihydroxyphenyl)-2-methylalaninate
(+)-Tartaric Acid/Phosphoric Acid (3/1)
Monohydrate Salts 33.9 grams (0.1 mole, 99.5 percent purity) of (R,S)-POE ester base in 800 milliliters of ethyl acetate was stirred at room temperature for 15 minutes and the mixture filtered to remove impurities. The filtered solid was washed with two 15 milliliter portions of ethyl acetate and the ethyl acetate solutions combined. To the combined solution there was added 1 gram of a previously prepared (R,S)-POE-(+)-tartaric acid salt as seed, followed by a slow addition of 11.25 grams (0.075 mole) of (+)-tartaric acid in 10 milliliters of water. The addition funnel was rinsed with 3 milliliters of water into the mixture and the mixture then stirred at ambient temperature for about 2 hours whereupon crystals comprising primarily of the salts of the S-isomer separated in the reaction mixture. To the resulting mixture, an additional gram of (R,S)-POE ester (+)-tartaric acid salt in 70 milliliters of ethyl acetate was added as seed and the mixture cooled by a circulating ethylene glycol bath whereupon crystallization of the R-isomer salt took place. After aging overnight at about −12° C. substantially equal amounts of the R- and S-isomer was found to have formed. (An estimate of the ratio was made by thin layer chromatography employing 60:25:10:5 EtOAc:n-BuOH:HCOOH:$H_2O$; system on silica gel plates with $I_2$ visualization. The Rf for S-isomer was 0.6 and R-isomer, 0.7).

To the crystallization mixture containing R and S tartrate salts of POE ester base, there was added a solution of 1.7 milliliters of 85 percent phosphoric acid in 3 milliliters of water and 100 milliliters of ethyl acetate containing 0.5 gram of (R,S)-POE ester phosphate salt seeds, and stirring continued at −12° C. for additional 16–20 hours whereupon R and S phosphate salts of POE ester base crystallized. The mixed crystals were then recovered by filtration and washed with two 25 milliliter portions of cold ethyl acetate and dried at 25° C./1 mm to obtain (R,S)-1-pivaloyloxyethyl (S)-3-(3,4-dihydroxyphenyl)-2-methylalaninate (+)-tartaric acid/phosphoric acid (3:1) monohydrate salt in a yield of 44 grams (90 percent of theoretical). The product had a melting temperature of 122.5° $\propto$ 128.5° (dec). Elemental analysis for phosphorus and other analytical information are as follows:

Elemental for P: Calculated P, 1.70. Found P, 1.74
KF 3.0 percent
UV 280 nm A%=56.4
Titration ($HClO_4$ and NaOH)
72.4 percent POE Tartrate salts (uncorr.);
24.2 percent POE Phosphate salts (uncorr.);
99.5 percent POE Ester (corrected for KF)
Equivalent weight=492.3 ($HClO_4$)

LC 67.3 weight percent as (R,S)-POE ester base; 97.6 percent pure as tartrate and phosphate salts hydrate; 0.3 percent α-methyldopa Microscopy: Crystalline material, <10μ with agglomerates; exhibits birefringence.

EXAMPLE 5

(R,S)-1-Pivaloyloxyethyl (S)-3-(3,4-Dihydroxyphenyl)-2-methylalaninate (+)-Tartaric Acid Monohydrate Salts 33.9 grams (0.1 mole, 98 percent purity) of (R,S)-POE ester base in 625 milliliters of ethyl acetate was stirred under nitrogen at 20°–25° C. for about 20 minutes then filtered to remove insoluble impurities. The filtrate was washed with two 50 milliliter portions of ethyl acetate, the ethyl acetate solutions combined and then diluted with additional 250 milliliters of ethyl acetate. To the resulting solution while under nitrogen atmosphere was added a solution of 15 grams (0.1 mole) of (+)-tartaric acid in 25 milliliters of water and the solution seeded with 2.4 grams of previously prepared (R,S)-POE ester (+)-tartaric acid salt mixture whereupon crystallization began. Stirring was continued for about 2 hours at room temperature with separation predominantly of the salt of the S-isomer.

At the end of this period, the mixture was diluted with 1000 milliliters of ethyl acetate, cooled to 0° C. over a 2 hour period, seeded with additional 2.4 grams of (R,S)-POE ester (+)-tartaric acid salt mixture and maintained at 0° C. for about 4 hours to obtain white, crystalline (R,S)-1-pivaloyloxyethyl (S)-3-(3,4-dihydroxyphenyl)-2-methylalaninate (+)-tartaric acid monohydrate salts in a yield of 42.0 grams (after correction for seed crystals) or 86 percent of theoretical.

Elemental analyses and rotation properties of the product were as follows:

Calculated for: $C_{17}H_{25}NO_6 \cdot C_4H_6O_6 \cdot H_2O$ (507.5): Calcd.: C, 49.70; H, 6.55; N, 2.76. Found: C, 49.35; H, 6.34; N, 2.59.

Rotation: $[\alpha]_{365}^{25} = +8.9°$ (C=5, $H_2O$)*

*Isomer ratio: 56 percent-S-isomer; 44 percent-R-isomer based on a rotation of +31.3° for the pure S-isomer and −18.9° for the pure R-isomer under the same conditions.

EXAMPLE 6

(R,S)-1-Pivaloyloxyethyl (S)-3-(3,4-Dihydroxyphenyl)-2-methylalaninate, Phosphoric Acid, Monoisopropanolate Salts In an operation carried out in a manner similar to that described in Example 1, 42.3 grams (0.2 mole) of methyldopa, 40.3 milliliters (0.24 mole) of 1-chloroethyl pivalate, 14 grams of 4A molecular sieve pellets (1/16") and 85 milliliters of tetramethylurea are mixed together and heated in an atmosphere of nitrogen to 70° C. and maintained at this temperature for about 30 hours. During this time, the methyldopa dissolves with the formation of (R,S)-1-pivaloyloxyethyl ester product. Thereafter, the reaction mixture is cooled to 25° C. and diluted with 380 milliliters of toluene. The mixture is then washed with three 500 milliliter portions of saturated sodium bicarbonate solution and filtered to clarify the solution. To this solution is added 300 milliliters of isopropanol followed by 16.6 grams (0.14 mole) of 85 percent phosphoric acid and 0.100 gram of methyldopa (R,S)-POE ester phosphoric acid monoisopropanolate seed whereupon the product crystallizes. The crystal-containing slurry is aged for 16 hours at 20°–25° C., then filtered and washed with two 75 milliliter portions of isopropanol and dried in vacuo to obtain (R,S)-1-pivaloyloxyethyl (S)-3-(3,4-dihydroxyphenyl)-2-methylalaninate, phosphoric acid, monoisopropanolate salt.

EXAMPLE 7

(R,S)-1-Pivaloyloxyethyl (S)-3-(3,4-Dihydroxyphenyl)-2-methylalaninate, Phosphoric Acid, Monoisopropanolate Salts 10 grams (0.03, 96 percent purity) of (R,S)-POE ester base was added to a mixture of 100 milliliters of isopropanol, 3 grams of 85 percent phosphoric acid and 3 milliliters of water. The mixture slurry was seeded with a small amount of previously prepared POE ester, phosphoric acid isopropanolate salt whereupon immediate heavy precipitation of (R,S)-1-pivaloyloxyethyl (S)-3-(3,4-dihydroxyphenyl)-2-methylalaninate, phosphoric acid, isopropanolate salt product precipitated as crystalline white powder. Optical rotation of the mixture was $[\alpha]_{365}^{25} = -11.3°$ (C=1.0, $H_2O$), indicating about 54 percent of S-isomer and 46 percent of the R isomer.

EXAMPLE 8

(R,S)-1-Pivaloyloxyethyl (S)-3-(3,4-Dihydroxyphenyl)-2-methylalaninate, Maleic Acid, Monoethanolate Salts In a manner similar to that described in Example 1 and 6, a mixture of 21.2 grams (0.10 mole) of methyldopa, 20.15 milliliters (0.12 mole) of 1-chloroethyl pivalate, 7 grams of 4A molecular sieve (1/16" pellets) and 43 milliliters of tetramethylurea are heated to 70° C. and maintained at this temperature for 30 hours under an atmosphere of nitrogen. During this period a reaction takes place with dissolution of methyldopa and formation of the R,S-POE ester of methyldopa. The mixture is allowed to cool to 25° C. and then diluted with 205 milliliters of toluene. It is then washed with three 250 milliliter portions of saturated aqueous sodium bicarbonate solution. The organic layer after separation from the aqueous layer is clarified by filtration and diluted with 125 milliliters of ethanol. A solution of 8.12 grams (0.7 mole) of maleic acid in 20 milliliters of ethanol and 0.1 gram of a previously prepared maleic acid, monoethanolate salt as seed is added whereupon maleic acid monoethanolate salt of R,S-POE ester of methyldopa begins to precipitate as crystals. The mixture is aged for about 16 hours at 20°–25° C. to complete the formation of crystals and then filtered to recover the solid product. The product is washed with 250 milliliter portions of ethanol and dried in vacuo to obtain purified (R,S)-1-pivaloyloxyethyl (S)-3-(3,4-dihydroxyphenyl)-2-methylalaninate, maleic acid, monoethanolate salt.

EXAMPLE 9

(R,S)-1-Pivaloyloxyethyl (S)-3-(3,4-dihydroxyphenyl)-2-methylalaninate, Phosphoric Acid, Monomethanolate Salts In a similar operation similar to that described in Example 2 under an atmosphere of nitrogen, 200 grams of methyldopa, R,S-POE ester (of 97 percent purity) and 68 grams of 1400 milliliters of toluene and 700 milliliters of methanol at 21° C. to obtain a light amber colored organic solution. The solution is seeded with 0.5 gram of a previously prepared POE ester phosphoric acid methanolate salt whereupon crystal formation starts with the precipitation of the salt product crystals in the reaction mixture. The mixture is allowed to stand for about 16 hours at temperature range of 20°–25° C. to complete the formation of the crystals of (R,S)-1-pivaloyloxyethyl(S)-3-(3,4-dihydroxyphenyl)-2-methylalaninate, phosphoric acid, monomethanolate salt product. The product is washed with two 500 milliliter portions of methanol and dried in vacuo to obtain a purified product.

EXAMPLE 10

(R,S)-1-Pivaloyloxyethyl (S)-3-(3,4-dihydroxyphenyl)-2-methylalaninate, Sulfuric Acid, Monoethanolate Salts In a similar manner, under a nitrogen atmosphere, a mixture of 200 grams of methyldopa, R,S-POE ester (of 97 percent purity) and 31 grams of concentrated sulfuric acid are added portionwise to a mixture of 1400 milliliters of toluene and 700 milliliters of ethanol at about 20° C. The resulting mixture is seeded with 0.5 gram of crystalline POE ester sulfuric acid ethanolate salt whereupon crystals start to separate immediately in the reaction mixture. The crystalline slurry is allowed to stand in the temperature range of 20°–25° C. for 16 hours and thereafter filtered, washed with two 600 milliliter portions of ethanol and dried in vacuo to produce (R,S)-1-pivaloyloxyethyl(S)-3-(3,4-dihydroxyphenyl)-2-methylalaninate, sulfuric acid, monoethanolate salt product.

EXAMPLE 11

(R,S)-1-Pivaloyloxyethyl (S)-3-(3,4-Dihydroxyphenyl)-2-methylalaninate, Phosphoric Acid, Monoisopropanolate Salts To a slurry of 10.2 grams of methyldopa, R,S-POE ester in 100 milliliters of isopropanol was added 3.5 grams of 85 percent phosphoric acid, followed by 1 milliliter of water which produced a solution. The mixture was stirred for 4 hours at 25° C. whereupon a heavy crystalline precipitate formed. The mixture was maintained at 0°–5° C. overnight and then filtered and washed with two 50 milliliter portions of isopropanol to obtain 13.2 grams of (R,S)-1-pivaloyloxyethyl (S)-3-(3,4-dihydroxyphenyl)-2-methylalaninate, phosphoric acid, monoisopropanolate salt product as a white solid.

Analytical results were as follows:

KF=1.62 percent
Titration (HClO$_4$)=93.5% uncorr.
$[\alpha]_{365}^{25}$ nm = −14.0°
X-ray = crystalline/none crystalline
Elemental analyses: Calc'd. for $C_{17}H_{25}NO_6 \cdot H_3PO_4 \cdot H_2O$ (m.w. 455); C, 44.84; H, 6.64; N, 3.08; P, 6.80. Found: C, 46.79; H, 7.29; N, 2.80; P, 4.50.

EXAMPLE 12

In an operation similar to that described in Examples 7 and 11, (R,S)-1-pivaloyloxyethyl (S)-3-(3,4-dihydroxyphenyl)-2-methylalaninate, phosphoric acid, monoethanolate salts are prepared by mixing together 10 grams of R,S-POE ester base, 3 grams of 85 percent phosphoric acid and 100 milliliters of ethanol at ambient temperature, then maintaining overnight at 0°–5° C. and recovering by filtration.

PREPARATION OF STARTING MATERIAL

The (R,S)-1-pivaloyloxyethyl (S)-3-(3,4-dihydroxyphenyl)-2-methylalaninate starting material is known in the art and also may be prepared by intimately mixing with warming (S)-2-(3,4-dihydroxyphenyl)-2-methylalanine with 1-chloroethyl pivalate in an aprotic solvent such as dimethylsulfoxide or tetramethylurea in the absence of an acid binding agent according to the method more fully described in U.S. Pat. No. 3,988,341 or by the hydrogenation method described in the aforecited J. Med. Chem. 21, 746 (1978). It also may be prepared following the procedure of Example 1A.

What is claimed is:

1. A process for preparing in substantially crystalline form, a diastereomeric salt mixture of 1-pivaloyloxyethyl ester of (S)-3-(3,4-dihydroxyphenyl)-2-methylalanine with an inorganis acid and obtained as an alkanolate which comprises mixing together to form a slurry and causing to react purified (R,S)-1-pivaloyloxyethyl (S)-3-(3,4-dihydroxyphenyl)-2-methylalaninate, the appropriate inorganic acid for the desired salt and lower alkanol in the absence of a water-immiscible solvent.

2. A process according to claim 1 in which the acid is phosphoric acid and the alkanol is ethanol.

3. A process according to claim 1 in which the acid is phosphoric acid and the alkanol is isopropanol.

* * * * *